United States Patent
Musca et al.

(10) Patent No.: US 12,064,542 B2
(45) Date of Patent: Aug. 20, 2024

(54) APPARATUS, SYSTEM AND DATA CARRIER FOR AUTOMATED PERITONEAL DIALYSIS TREATMENT

(71) Applicant: Fresenius Medical Care Deutschland GmbH, Bad Homburg (DE)

(72) Inventors: Gheorghe Musca, Bucharest (RO); Ariana Popescu, Bucharest (RO)

(73) Assignee: FRESENIUS CARE DEUTSCHLAND GMBH, Bad Homburg (DE)

( * ) Notice: Subject to any disclaimer, the term of this patent is extended or adjusted under 35 U.S.C. 154(b) by 795 days.

(21) Appl. No.: 17/271,299

(22) PCT Filed: Aug. 27, 2019

(86) PCT No.: PCT/EP2019/072870
§ 371 (c)(1),
(2) Date: Feb. 25, 2021

(87) PCT Pub. No.: WO2020/043733
PCT Pub. Date: Mar. 5, 2020

(65) Prior Publication Data
US 2021/0178044 A1   Jun. 17, 2021

(30) Foreign Application Priority Data
Aug. 28, 2018   (EP) .................................. 18465567

(51) Int. Cl.
*A61M 1/28* (2006.01)
*G16H 20/40* (2018.01)
*G16H 40/63* (2018.01)

(52) U.S. Cl.
CPC ............. *A61M 1/282* (2014.02); *A61M 1/287* (2013.01); *G16H 20/40* (2018.01); *G16H 40/63* (2018.01);
(Continued)

(58) Field of Classification Search
CPC .................. A61M 1/282; A61M 1/287; A61M 2202/0486; A61M 2205/3379;
(Continued)

(56) References Cited

FOREIGN PATENT DOCUMENTS

| EP | 3290069 | 8/2017 |
|----|---------|--------|
| WO | WO97/07837 | 3/1997 |

*Primary Examiner* — John Kim
(74) *Attorney, Agent, or Firm* — Jacobson Holman PLLC

(57) ABSTRACT

The present invention relates to an apparatus for performing an automated peritoneal dialysis treatment on a patient, the apparatus comprising: a first dialysis fluid port for receiving a first dialysis fluid having a first composition, which is determined by the concentrations of a set of first dialysis fluid constituents; a dialysis fluid line system connecting the first dialysis fluid port to a patient terminal; at least one dialysis fluid pump acting on the dialysis fluid line system and configured to convey the first dialysis fluid from the first dialysis fluid port to the patient terminal; and a control unit operably connected to the at least one pump; wherein the apparatus further comprises a second dialysis fluid port for receiving a second dialysis fluid having a second composition, which is determined by the concentrations of a set of second dialysis fluid constituents. The invention further relates to a system for automated peritoneal dialysis treatment and a data carrier comprising controlling software for such apparatus or system.

15 Claims, 2 Drawing Sheets

(52) U.S. Cl.
CPC ........... *A61M 2202/0486* (2013.01); *A61M 2205/3379* (2013.01); *A61M 2205/50* (2013.01); *Y02A 90/10* (2018.01)

(58) Field of Classification Search
CPC ... A61M 2205/50; G16H 20/40; G16H 40/63; Y02A 90/10
See application file for complete search history.

APPARATUS, SYSTEM AND DATA CARRIER FOR AUTOMATED PERITONEAL DIALYSIS TREATMENT

The invention relates to an apparatus and system for automated peritoneal dialysis treatment, the apparatus and system using at least two different dialysis fluids and a non-standard inflow profile to apply an overall volume dialysis fluid of variable composition to a patient. The invention further relates to a data carrier comprising controlling software for such apparatus or system.

Prescriptions for peritoneal dialysis patients may be tailor-made under consideration of a variety of patient-specific parameters. These prescriptions may comprise detailed information for each inflow-dwell-outflow cycle, such as the composition of the dialysis fluid to be used, in particular the concentration of one or more dialysis fluid constituents, the fill volume, the fill rate and duration of the inflow phase, the duration of the dwell phase, etc. To obtain an optimal treatment performance, an automated peritoneal dialysis treatment should comply with the prescription as closely as possible.

It follows from the above that the prescription determines the composition and amount of the dialysis fluids to be used for each inflow-dwell-outflow cycle, and these compositions and amount can vary from cycle to cycle. Hence, a large variety of dialysis fluid bags need to be made available for optimal supply to a number of patients.

The invention aims to provide an apparatus and system for performing an automated peritoneal dialysis treatment on a patient, where a large variety of prescriptions can be realized with a reduced variety of dialysis fluid bags.

Against this background, as shown in FIG. 2 the invention relates to an apparatus 1 for performing an automated peritoneal dialysis treatment on a patient, the apparatus comprising: a first dialysis fluid port 3 for receiving a first dialysis fluid having a first composition, which is determined by the concentrations of a set of first dialysis fluid constituents; a dialysis fluid line system connecting the first dialysis fluid port 3 to a patient terminal 5; at least one dialysis fluid pump 7 acting on the dialysis fluid line system and configured to convey the first dialysis fluid from the first dialysis fluid port to the patient terminal; and a control unit 9 operably connected to the at least one pump 7; wherein the apparatus further comprises a second dialysis fluid port 11 for receiving a second dialysis fluid having a second composition, which is determined by the concentrations of a set of second dialysis fluid constituents, wherein the second composition differs from the first composition in the concentration of at least one particular constituent, the first composition having a first concentration C1 of that particular constituent and the second composition having a second concentration C2 of that particular constituent; wherein also the second port 11 is connected to the patient terminal 5 by the dialysis fluid line system and the or another dialysis fluid pump acting on the dialysis fluid line system and operably connected to the control unit is configured to convey the second dialysis fluid from the second dialysis fluid port to the patient terminal; and wherein the control unit is configured to apply a first volume V1 of the first dialysis fluid and a second volume V2 of a second dialysis fluid to the patient in the course of a multi-step inflow phase, wherein the first and second volumes V1 and V2 are determined based on a prescription that defines a target concentration C for the particular constituent, which lies in between the first and second concentrations C1 and C2 of the first and second dialysis fluids for the particular constituent, to obtain the target concentration C in the overall volume V applied to the patient during the multi-step inflow phase.

The first and/or the second dialysis fluid ports are preferably configured to detachably connect to separate first and second dialysis fluid sources comprising the first and second dialysis fluids.

Figure 1:
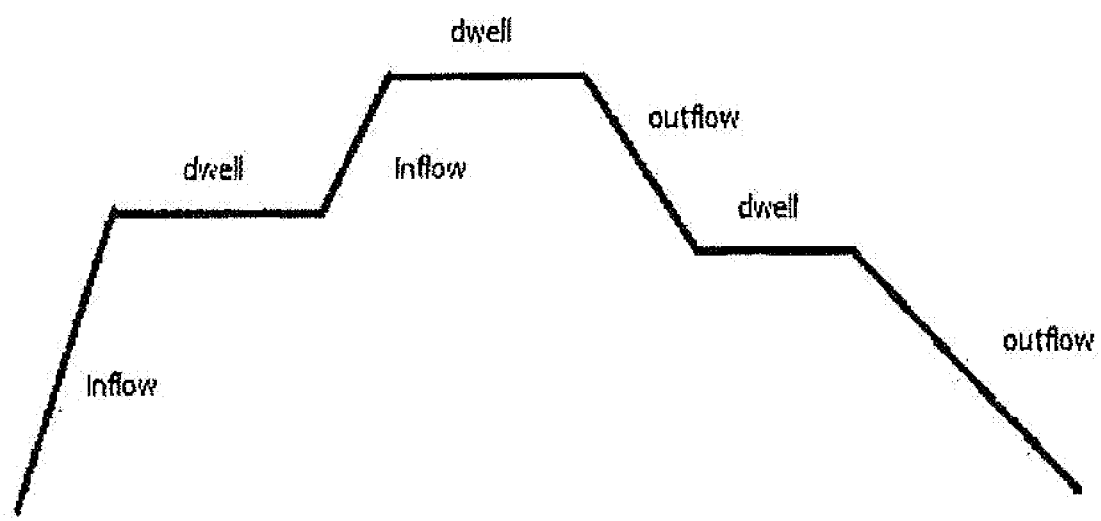
FIG. 1 exemplifies an automated peritoneal dialysis treatment profile according to the invention.
Figure 2:
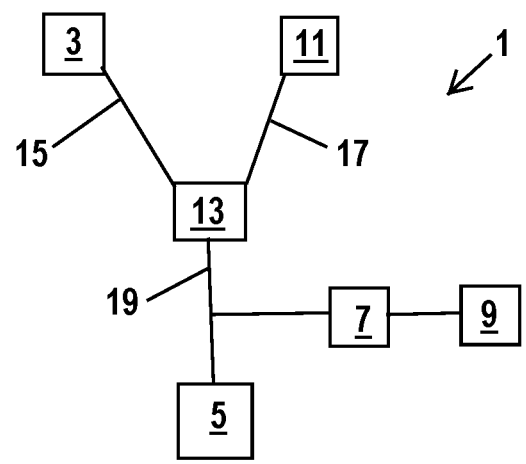
FIG. 2 schematically exemplifies an apparatus according to the invention.

According to the present invention, only two dialysis fluids having two different concentrations of at least one particular constituent are necessary to obtain any desired target concentration of this particular constituent in a patient, and this target concentration can vary between every inflow-dwell-outflow cycle. The only precondition is that the target concentration of the particular constituent lies between the concentrations of this constituent in the first and second dialysis fluid solutions. The concentration C1 or C2 of the particular constituent in the first or second dialysis solution may also be zero, but not both concentrations C1 and C2 may be 0 at the same time.

Typical overall fill volumes V are in the range of between 1.5 to 3.5 litres, preferably 2.0 to 2.5 litres. Typical inflow rates for each of the two or more inflow sub-phases of the multi-step inflow phase are individually in the range of between 5 to 350 ml/min. The duration of the sum of the two or more inflow sub-phases of the multi-step inflow phase is dependent on the applied inflow rates and the overall fill volume and is typically in the range of between 5 to 30 minutes, preferably 5 to 20 minutes, more preferably 10 to 15 minutes. The above values apply to grown-up patients, for paediatric treatment some values, in particular the fill volume, may need to be adjusted.

In one embodiment, the apparatus comprises only the two dialysis fluid ports and wherein the overall volume V of dialysis fluid applied to the patient during the multi-step inflow phase corresponds to the sum V1+V2 of the first and second volume. The multi-step inflow phase may comprise only two steps, one step of applying the first volume V1 of the first dialysis fluid and a second step of applying second volume V2 of a second dialysis fluid to the patient. The volumes V1 and/or V2 could, however, also be distributed over more than one step.

In one embodiment, at least two steps of the multi-step inflow phase are interrupted by an intermediate dwell phase to obtain an inflow-dwell-inflow profile. This intermediate dwell could also be used to realize a particular prescription that is advantageous for the treatment of a patient.

Generally, the apparatus for performing an automated peritoneal dialysis treatment according to the invention may comprise profiling capabilities to run inflow, dwell and outflow phases in any order, not just the standard inflow-dwell-outflow sequence.

The particular constituent is an osmotic, preferably glucose or a glucose derivative. The invention may be particularly useful to realize prescriptions where different osmotic concentrations are envisaged for the different cycles. The prescribed osmotic concentration of the dialysis fluid, in particular upon use of glucose as an osmotic, may typically be in the range of between 1.25 and 4.50 wt.-%, preferably 1.50 to 4.25 wt.-%.

Other embodiments may use different sodium concentrations for the different cycles or specific additives for specific cycles.

In one embodiment, the first and second compositions of the first and second dialysis fluids differ only in the concentration of the one particular constituent. The concentration of this particular constituent, for example the osmotic concentration, in the overall volume of dialysis fluid applied to the patient during the inflow-dwell-outflow cycle could hence be freely varied without any collateral amendments to any other fluid constituents.

The dialysis fluid line system may comprise an Y-junction 13 where a first feed line 15 connected to the first dialysis fluid port 3 and a second feed line 17 connected to the second dialysis fluid port 11 combine into a common feed line 19 connected to the patient terminal.

The apparatus may comprise only one dialysis fluid pump acting on the common feed line and configured to convey both the first dialysis fluid and the second dialysis fluid from the respective dialysis fluid ports to the patient terminal.

In one embodiment, the apparatus comprises a 3/2-way valve arranged at the Y-junction and operably connected to the control unit, wherein the valve enables inhibiting a flow of the second dialysis fluid from the second to the common feed line while enabling a flow of the first dialysis fluid from the first to the common feed line, and wherein the valve enables inhibiting a flow of the first dialysis fluid from the first to the common feed line while enabling a flow of the second dialysis fluid from the second to the common feed line. The valve may, for example, be a 3/2-way magnetic valve.

In some embodiments, the apparatus may also be configured to use three or more dialysis fluids having distinct compositions to realize more complicated prescriptions. Each of the elements described above, such as the dialysis fluid ports, the dialysis fluid lines, the junctions and valves and the control unit may be present three- or more-fold and/or configured to accommodate the use of three or more different dialysis fluids having three or more different compositions.

The apparatus may comprise a user interface or receiving interface to obtain information on a certain prescription.

The invention further relates to a system for performing an automated peritoneal dialysis treatment on a patient, the system comprising: an apparatus according to the invention; and first and second dialysis fluid sources comprising the first and second dialysis fluids, said first and second dialysis fluid sources being connected to the first and second ports. The first and second dialysis fluid sources are preferably dialysis fluid receptacles, more preferably dialysis fluid bags.

The invention further relates to a data carrier comprising controlling software for an apparatus or system according to the invention. The controlling software is preferably configured to apply a first volume V1 of the first dialysis fluid and a second volume V2 of a second dialysis fluid to the patient in the course of a multi-step inflow phase, wherein the first and second volumes V1 and V2 are determined based on a prescription that defines a target concentration C for the particular constituent, which lies in between the first and second concentrations C1 and C2 of the first and second dialysis fluids for the particular constituent, to obtain the target concentration C in the overall volume V applied to the patient during the multi-step inflow phase. Advantageous embodiments become apparent from the description of the apparatus or system according to the invention.

The controlling software may be configured to establish a prescription for automated peritoneal dialysis, in which a predetermined volume V and a predetermined concentration C for any dialysis fluid constituent within a range [C1, C2] may individually be selected for every cycle of the automated peritoneal dialysis treatment, wherein C1 corresponds to the concentration of said dialysis fluid constituent in one dialysis fluid reservoir and C2 corresponds to the concentration of said dialysis fluid constituent in another dialysis fluid reservoir. D1 may be a minimum value Cmin and C2 may be a maximum value Cmax. The software may hence generate inflow sequences {Vi, Ci}, I=1, 2, etc. for an apparatus and system of the invention. The controlling software may be configured to establish the prescription on the basis of a user input comprising information on the intended equivalent volume and the intended equivalent concentration of the dialysis treatment.

The clinical software may hence be able to prescribe a variable concentration C of a certain fluid. The clinical user prescribes the equivalent volume V and concentration C for a certain APD cycle and the software generated sequences of inflow phases (V1, C1) and (V2, C2), more general: inflow sequences $\{V_i, C_i\}_{i=1, 2, 3, \ldots}$, calculated so that SUM (Vi)=V and SUM (Vi×Ci)=V×C.

Further details and advantages of the invention are described with reference to the working examples below.

An exemplary apparatus for performing an automated peritoneal dialysis treatment according to the invention comprises profiling capabilities to run inflow, dwell and outflow phases in any order, not just the standard inflow-dwell-outflow sequence.

FIG. 1 shows an example of such non-standard treatment profile, comprising, inter alia, an inflow-dwell-inflow sequence.

The exemplary apparatus is configured according to the invention and comprises first and second dialysis fluid ports for receiving first and second dialysis fluids, which are identical except for different concentrations of the osmotic glucose. A dialysis line system connects both dialysis fluid ports to a patient terminal and a dialysis fluid pump acts on the dialysis fluid line system to sequentially convey defined amounts the first and second dialysis fluids from the ports to the patient terminal.

A control unit operably connected to the pump and the line system is configured to apply a first volume V1 of the first dialysis fluid and a second volume V2 of a second dialysis fluid to a patient in the course of a two-step inflow phase as shown in FIG. 1. The first and second volumes V1 and V2 are applied based on a prescription that is stored on the control unit and defines a target concentration C for the glucose in the overall volume V applied to the patient.

Specifically, the sequence of the two inflow phases INFLOW-1 and INFLOW-2 is equivalent to a single inflow phase, in which the equivalent inflow volume V is the sum of the two inflow volumes V1 and V2 of the inflow phases INFLOW-1 and INFLOW-2, respectively, in which the equivalent inflow time T is the sum of the two inflow times T1 and T2 of the inflow phases INFLOW-1 and INFLOW-2, respectively, and in which the equivalent flow rate Q is (Q1×V1+Q2×V2)/(V1+V2), in which Q1 and Q2 are the flow rates during the inflow phases INFLOW-1 and INFLOW-2, respectively. If Q1=Q2, then Q=Q1=Q2.

Likewise, the sequence of the two inflow phases INFLOW-1 and INFLOW-2 with different glucose concentrations C1 and C2, respectively, and volumes V1 and V2, respectively, is equivalent to a single inflow phase, with an equivalent glucose concentration $C=(C1\times V1+C2\times V2)/(V1+V2)$.

If the prescription provides for an equivalent glucose concentration C of 2.30 wt.-%, for example, and an equivalent volume V of 2.25 litres, for example, during the main dwell phase, and if there are two otherwise identical dialysis fluids available at the ports, one having a glucose concentration of 1.50 wt.-% and the other having a glucose concentration of 4.25 wt.-%, the control unit may determine the volumes V1 and V2 necessary as follows:

$V1+V2=2.25$ litres $V1\times 1.50$ wt.-%$+V2\times 4.25$ wt.-%$=2.25$ litres$\times 2.30$ wt.-%

By substitution:

$V1\times 1.50$ wt.-%$+(2.25$ litres$-V1)\times 4.25$ wt.-%$=2.25$ litres$\times 2.30$ wt.-%

Resulting in:

$V1=1.60$ litres $V2=0.65$ litres

Hence, to realize such prescription, the apparatus would apply to the patient 1.60 litres of the first dialysis fluid having a glucose concentration of 1.50 wt.-% during one inflow sub-phase of the inflow-dwell-inflow phase and 0.65 litres of the second dialysis fluid having a glucose concentration of 4.25 wt.-% during the other inflow sub-phase of the inflow-dwell-inflow phase in the course of the two-step inflow phase as shown in FIG. 1.

The glucose concentrations C1 and C2 of the first and second dialysis fluids could be freely chosen to optimize the average balance between volumes V1 and V2, so that the total number of solution bags needed for therapy is minimized.

The invention claimed is:

1. An apparatus for performing an automated peritoneal dialysis treatment on a patient, the apparatus comprising:
a first dialysis fluid port for receiving a first dialysis fluid having a first composition, which is determined by the concentrations of a set of first dialysis fluid constituents;
a dialysis fluid line system connecting the first dialysis fluid port to a patient terminal;
one dialysis fluid pump acting on the dialysis fluid line system and configured to convey the first dialysis fluid from the first dialysis fluid port to the patient terminal; and
a control unit operably connected to the dialysis fluid pump;
characterized in that
the apparatus further comprises a second dialysis fluid port for receiving a second dialysis fluid having a second composition, which is determined by the concentrations of a set of second dialysis fluid constituents, wherein the second composition differs from the first composition in the concentration of at least one particular constituent, the first composition having a first concentration C1 of that particular constituent and the second composition having a second concentration C2 of that particular constituent;
wherein also the second dialysis fluid port is connected to the patient terminal by the dialysis fluid line system and the dialysis fluid pump acting on the dialysis fluid line system and operably connected to the control unit is configured to convey the second dialysis fluid from the second dialysis fluid port to the patient terminal; and
wherein the control unit is configured to control the dialysis fluid pump to apply a first volume V1 of the first dialysis fluid and a second volume V2 of a second dialysis fluid to the patient in the course of a multi-step inflow phase, wherein the first and second volumes V1 and V2 are determined based on a prescription that defines a target concentration C for the particular constituent, which lies in between the first and second concentrations C1 and C2 of the first and second dialysis fluids for the particular constituent, to obtain the target concentration C in the overall volume V applied to the patient during the multi-step inflow phase, wherein the dialysis fluid line system comprises a Y-junction where a first feed line connected to the first dialysis fluid port and a second feed line connected to the second dialysis fluid port combine into a common feed line connected to the patient terminal, wherein the apparatus comprises only one dialysis fluid pump acting on the common feed line and configured to convey both the first dialysis fluid and the second dialysis fluid from the respective dialysis fluid ports to the patient terminal.

2. The apparatus of claim 1, wherein the apparatus comprises only the two dialysis fluid ports and wherein the overall volume V of dialysis fluid applied to the patient during the multi-step inflow phase corresponds to the sum V1+V2 of the first and second volume.

3. The apparatus of claim 1, wherein at least two steps of the multi-step inflow phase are interrupted by an intermediate dwell phase to obtain an inflow-dwell-inflow profile.

4. The apparatus of claim 1, wherein the particular constituent is an osmotic.

5. The apparatus of claim 1, wherein the first and second compositions of the first and second dialysis fluids differ only in the concentration of the one particular constituent.

6. The apparatus of claim 1, wherein the apparatus comprises a 3/2-way valve arranged at the Y-junction and operably connected to the control unit, wherein the valve enables inhibiting a flow of the second dialysis fluid from the second dialysis fluid port to the common feed line while enabling a flow of the first dialysis fluid from the first dialysis fluid port to the common feed line, and wherein the valve enables inhibiting a flow of the first dialysis fluid from the first dialysis fluid port to the common feed line while enabling a flow of the second dialysis fluid from the second dialysis fluid port to the common feed line.

7. The apparatus of claim 1, wherein the particular constituent is glucose or a glucose derivative.

8. A system for performing an automated peritoneal dialysis treatment on a patient, the system comprising:
an apparatus according to claim 1; and
first and second dialysis fluid sources comprising the first and second dialysis fluids, said first and second dialysis fluid sources being connected to the first and second ports.

9. The system of claim 8, wherein the first and second dialysis fluid sources are dialysis fluid receptacles.

10. The system of claim 8, wherein the first and second dialysis fluid sources are dialysis fluid bags.

11. A data carrier comprising controlling software for an apparatus according to claim 1.

12. The data carrier of claim 11, wherein the controlling software is configured to apply a first volume V1 of the first dialysis fluid and a second volume V2 of a second dialysis fluid to the patient in the course of a multi-step inflow phase, wherein the first and second volumes V1 and V2 are determined based on a prescription that defines a target concentration C for the particular constituent, which lies in between the first and second concentrations C1 and C2 of the first and second dialysis fluids for the particular constituent, to obtain the target concentration C in the overall volume V applied to the patient during the multi-step inflow phase.

13. The data carrier of claim 11, wherein the controlling software is configured to establish a prescription for automated peritoneal dialysis, in which a predetermined volume V and a predetermined concentration C for any dialysis fluid constituent within a range [C1, C2] may individually be selected for every cycle of the automated peritoneal dialysis treatment, wherein C1 corresponds to the concentration of said dialysis fluid constituent in one dialysis fluid reservoir and C2 corresponds to the concentration of said dialysis fluid constituent in another dialysis fluid reservoir.

14. The data carrier of claim 13, wherein the controlling software is configured to establish the prescription on the basis of a user input comprising information on the intended equivalent volume and the intended equivalent concentration of the dialysis treatment.

15. A data carrier comprising controlling software for a system according to claim 8.

* * * * *

UNITED STATES PATENT AND TRADEMARK OFFICE
CERTIFICATE OF CORRECTION

PATENT NO. : 12,064,542 B2
APPLICATION NO. : 17/271299
DATED : August 20, 2024
INVENTOR(S) : Gheorghe Musca Page 1 of 1

It is certified that error appears in the above-identified patent and that said Letters Patent is hereby corrected as shown below:

On the Title Page

Item (73) Assignee: please change "Fresenius Care Deutschland GmbH" to -- Fresenius Medical Care Deutschland GmbH --.

Signed and Sealed this
Twenty-fourth Day of December, 2024

Derrick Brent
*Acting Director of the United States Patent and Trademark Office*